(12) United States Patent
Huang

(10) Patent No.: US 9,816,928 B2
(45) Date of Patent: Nov. 14, 2017

(54) HUMAN BIOSENSORS FOR HEME BINDING

(71) Applicant: Tempo Bioscience, Inc., San Fransisco, CA (US)

(72) Inventor: Angela Huang, San Mateo, CA (US)

(73) Assignee: Tempo Bioscience Inc., San Francisco, CA (US)

( * ) Notice: Subject to any disclaimer, the term of this patent is extended or adjusted under 35 U.S.C. 154(b) by 0 days.

(21) Appl. No.: 15/361,379

(22) Filed: Nov. 26, 2016

(65) Prior Publication Data

US 2017/0146457 A1 May 25, 2017

Related U.S. Application Data

(63) Continuation-in-part of application No. 15/263,182, filed on Sep. 12, 2016, now Pat. No. 9,528,999, which is a continuation-in-part of application No. 14/469,218, filed on Aug. 26, 2014, now Pat. No. 9,587,230.

(60) Provisional application No. 61/873,950, filed on Sep. 5, 2013.

(51) Int. Cl.

| | |
|---|---|
| *G01N 21/64* | (2006.01) |
| *G01N 33/68* | (2006.01) |
| *G01N 33/72* | (2006.01) |
| *G01N 33/58* | (2006.01) |
| *C07K 14/00* | (2006.01) |

(52) U.S. Cl.
CPC ......... *G01N 21/6428* (2013.01); *C07K 14/00* (2013.01); *G01N 33/582* (2013.01); *G01N 33/6872* (2013.01); *G01N 33/721* (2013.01); *G01N 2021/6439* (2013.01)

(58) Field of Classification Search
CPC ........... G01N 21/6428; G01N 33/6872; G01N 33/721; G01N 33/582; G01N 2021/6439; C07K 14/00

See application file for complete search history.

(56) References Cited

U.S. PATENT DOCUMENTS

| | | |
|---|---|---|
| 8,653,037 B2 | 2/2014 | Shu |
| 2015/0080262 A1* | 3/2015 | Huang ..................... C12N 9/16 506/10 |

OTHER PUBLICATIONS

Fukuda M1, Nakano S, Tainaka K, Fujieda N, Morii T., Nucleic Acids Symposium Series No. 52 195-196 (2008); "Construction of a stable functional ribonucleopeptide complex by the covalent linking method".

* cited by examiner

*Primary Examiner* — Ruixiang Li
(74) *Attorney, Agent, or Firm* — Eric P. Mirabel

(57) ABSTRACT

This invention provides biosensors, cell models, and methods of their use for monitoring heme and oxygen. Biosensors can include targeting domains, sensing domains and reporting domains. Biosensors can be introduced into cells reprogrammed to represent experimental or pathologic cells of interest. Model cells expressing the biosensors can be contacted with putative bioactive agents to determine possible activities.

13 Claims, No Drawings ized
HUMAN BIOSENSORS FOR HEME BINDING

BACKGROUND

Detection of voltage potentials and changes to the internal ionic environment of cells can be useful in monitoring bioactivities of cells. For example, many cells experience significant changes in internal calcium ion ($Ca^{2+}$) concentration in response to binding of a ligand to a G-protein receptor. In another aspect, certain cells experience large changes in voltage potential across membranes, e.g., in response to contact with neurotransmitters at a synapse. Such cellular changes are responsible for important functions in cells and can be indicative of the health, function, or development processes of the cells.

Genetically encoded calcium indicators (GECI) have been developed to allow general monitoring of the $Ca^{2+}$ concentration in cells. See, e.g., Looger (U.S. 2012/0034691), wherein a calmodulin peptide sequence is combined in a construct with a green fluorescent protein (GFP) reporter. Conformational changes in the calmodulin peptide in response to $Ca^{2+}$ binding changes the efficiency of the GFP fluorescence, resulting in a change in the emissions profile and intensity. Cells transformed with the GECI can be monitored generally for changes in internal $Ca^{2+}$ concentration, e.g., in response to signaling ligands or inhibitors. Also see Griesbeck (U.S. 2009/0035788) wherein a FRET donor and acceptor are separated by a troponin peptide sequence, resulting in a fluorescence change on binding of $Ca^{2+}$. However, such GECIs are limited in their resolution of signal, limited in ability to penetrate multi-cell/3D structures, and in the range of available applicable cell types. Typically, the old art systems are directed to two dimensional microscopic detection of signals from a cell monolayer.

In many cases, signal transduction studies are carried out in cell types that are not representative of the actual cells of interest. For example, researchers may be limited to studying signaling agents and potential therapeutics in rodents or immortal cell lines in vitro, which often provide results not repeated in human cells, or clinical patients. For example, researchers can create host cells for study by introduction of oncogenes to primary cell lines, e.g., with differentiation to a cell type of choice. However, after this process history, the cells cannot be relied on to respond normally on contact with bioactive agents. Weiss (U.S. Pat. No. 7,101,709) discloses methods of preparing multipotent mouse neural stem cells. The cells could be differentiated and transplanted to somewhat immunoprivileged CNS locations. Again, the cells would be non-representative for many studies, and signal detection is limited to immunochemical means.

In view of the above, a need exists for model cell systems representative of cells and tissues existing in live animal systems of interest. It would be desirable to have sensor peptide constructs that can be targeted to specific intracellular locations. Benefits could be realized if systems were available allowing three dimensional signal detection in mock tissues of representative cells in vitro. The present invention provides these and other features that will be apparent upon review of the following.

SUMMARY

The present biosensors combine complementary features to detect intracellular changes associated with signaling in vivo. The present biosensors find utility in a variety of contexts. For example, the biosensors in human iPSCs-derived cell types can function to image 2D or 3D cellular models of in cells expressing certain pathologies. Such models can be useful in screening and evaluation of candidate drug compounds for chemical, biologic, therapeutic, and toxicological effects.

The synthetic and genetically encoded biosensors can function as reporters of calcium ($Ca^{2+}$) concentrations in human cells, voltage sensors, heme sensors or ATP sensors. The biosensors can have structures targeting cellular compartments, e.g., such as the nucleus, cytoplasm, plasma, certain membrane surfaces, and/or the like. The calcium biosensors can optionally function as reporters of cellular voltage changes in human cell compartments. For example, voltage sensors can evaluate and report fluctuations in membrane potentials due to differentials or changes in sodium ($Na^+$) and potassium ($K^+$) concentrations.

The biosensors can be configured to function in a cell-type specific manner. For example, biosensors can be genetically modified to contain promoter sequences specific to certain cell types, e.g., dopaminergic neurons, GABAergic neurons, astrocytes, cardiomyocytes, immortalized human cancer cell lines, HSCs, NPCs, human cells in general and/or MSCs.

In one embodiment, the biosensor is a voltage sensor. The voltage sensor can include, e.g., a peptide construct comprising a transmembrane domain, voltage sensitive domain, and a reporter domain. For example, the voltage sensor construct can include a transmembrane domain adapted to integrate into a membrane of a human cell, a voltage sensing domain sensitive to $H^+$, $Na^+$, and/or $K^+$ concentration, and a fluorescent reporter domain. The fluorescent reporter can be adapted to fluoresce at wavelengths in the range from 500 nm to 750 nm. The biosensor can be adapted to change conformation (e.g., in the voltage sensing domain) in response to local voltage potentials, resulting in the fluorescent reporter domain changing fluorescent emission characteristics. In many embodiments, the transmembrane domain and voltage sensing domain are different domains (e.g., having different non-homologous sequences, or being derived from different parent peptides).

In certain embodiments of the voltage sensor system, the voltage sensor peptide includes a voltage sensing domain comprising a sequence at least 70%, 80%, 90%, 95%, 98%, or 99% identical to: MSSVRYEQREEPSMVNGNFGN-TEEKVEIDGDVT APPKAAPRKSESVKKVHWND-VDQGPNGKSEVEEEERIDIPEISGLWWGENEHGVD DGRMEIPATWWNKLRKVISPFVMSFGFRVFGVVLI-IVDFVLVIVDLSVTDKSSGATT AISSISLAISFFFLIDI-ILHIFVEGFSQYFSSKLNIFDAAIVIVTLLVTLVYTV-LDAFTDFS GATNIPRMVNFLRTLRIIILVRIIILVRILRLASQKTISQN (SEQ ID NO: 1). In preferred embodiments, the voltage sensor peptide sequence retains I123, R220, R226, R229, R235 and/or R238 residues. In a more preferred embodiment, the voltage sensor domain peptide wherein the sequence retains at least R235 and I123.

In some embodiments of the voltage sensor system, the fluorescent reporter domain peptide includes a fluorescent domain comprising a sequence at least 70%, 80%, 90%, 95%, 98%, or 99% identical to: MVSKGEEDNMAIIKEF-MRFKVHMEGSVN GHQFKCTGEGEGRPYEAFQTAK-LKVTKGGPLPFAWDILSPQFMYGSRAFIKHPAGI PDFFKQSFPEGFTWERVTRYEDGGVVTVMQDTSLED (SEQ ID NO: 2).

In certain embodiments, the voltage sensor peptide construct includes the peptide sequences at least 70%, 80%, 90%, 95%, 98%, or 99% identical to each of SEQ ID NO: 1 and SEQ ID NO: 2.

Another inventive aspect includes a nucleic acid construct encoding any of the voltage sensors described herein. Further, the nucleic acid construct can comprise a tag sequence selected from the group consisting of: a nucleus localization signal (NLS) tag, a mitochondrial localization tag, and a ciliary tag. Further, the nucleic acid construct can include the NLS tag comprising at least 80% identity to the peptide sequence: DPKKKRKV (SEQ ID NO: 3).

Another aspect of the invention includes a human cell comprising the voltage sensor described herein. In preferred embodiments, the human cell is an iPSC derived cell. For example, the cell can be derived from induction of a fibroblast or a blood cell to a pluripotent or immortal status. In many cases, the cell is derived from a human patient derived cell type.

The inventions include methods of reprogramming and monitoring cells. For example, in a method of reprogramming fibroblasts can include transforming the fibroblasts with one or more constructs comprising a human clock gene and human Bmal1/2/3/4 genes having E-box promoters, synchronizing the circadian rhythm of the fibroblasts, modifying transcriptional regulatory control of the fibroblasts (thereby converting them into inducible pluripotent stem cells), and reprogramming the stem cells into inducible neurons (iN), glial cells (astrocytes included, iG), inducible pluripotent stem cells (iPSCs), or inducible neural progenitor cells (iNPCs). In many of the methods for reprogramming using circadian rhythms of human cell types, the transforming construct comprises a nucleic acid encoding a voltage sensor described herein or calcium sensor described herein.

The methods can include, e.g., modifying transcriptional control by providing specific transcription factors suitable for a lineage of the fibroblasts. The transcription factors can include the factors specific for a cellular lineage of the fibroblasts modified to include a circadian regulatory element (E-box promoters, an artificial E-box-like promoter sequence tag, a chemical agent that alters or synchronizes circadian rhythms cycles, or a synthetic transcriptional enhancer element) for reprogramming using circadian rhythms of human cell types.

The cellular composition can further include the co-culturing iN cells and iG cells to create a 3D model on a scaffold in vitro. Also, human cancer cell lines and cancer stem cells can be cultured in 3D spheroid manners using standard culturing hardware and conditions. Biosensor constructs of the invention can be used to image the resultant tissues and monitor changes in the cell voltage potentials and/or calcium levels, e.g., in real time.

The present inventive methods include compositions and techniques for screening agents that influence the voltage potential of cells. For example, methods for screening active agents can include transforming one or more cells with a nucleic acid encoding a voltage sensor, expressing the voltage sensor in the cells, contacting the cells with candidate active agents, and detecting a change in florescence of the voltage sensor in response to the agent. Typical agents can include, e.g., members of a small molecule chemical library. For example, the agents can be reviewed for an activity resulting from interactions with GPCR, a membrane channel, a receptor, and/or associated signaling pathways.

It is further envisioned that the methods are useful in imaging live cells in low, medium, and/or high throughput assay formats. For example, cells in 3D arrays, transformed and expressing biosensor constructs of the invention can be viewed in real time, e.g., using microscopic imaging systems. Optionally, biosensor cells in surface or suspension culture can be monitored using confocal imaging, FACS sorters, CCD video imaging, and/or the like.

3D human cancer cell models have been used as an improved predictor of tumor responses to drug candidates using library screening high throughput screening (HTS) methods. Cells used for such studies aren't limited to immortalized cancer cell lines. Cancer stem cells, primary tissue cells, and 3D printed tissue types can be used for screening.

DEFINITIONS

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a surface" includes a combination of two or more surfaces; reference to "bacteria" includes mixtures of bacteria, and the like.

Although any methods and materials similar or equivalent to those described herein can be used in the practice for testing of the present invention, the preferred materials and methods are described herein. In describing and claiming the present invention, the following terminology will be used in accordance with the definitions set out below.

iPSC refers to inducible pluripotent stem cells; iN refers to inducible neurons; iG refers to inducible glial cells (including astrocytes); and iNPCs inducible neural progenitor cells.

Near-Infrared refers to light wavelengths ranging from about 600 nm to about 1400 nm.

The term "conservative variant" includes modifications of given sequences that result in conserved function. For example, in the context of nucleic acids, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid.

Similarly, conservative variants in the context of peptide sequences can be expected to retain function. For example, Guo, "Protein Tolerance to Random Amino Acid Change", (PNAS 101:9205-10; 2004), demonstrates that one of skill can modify peptides successfully even "without detailed knowledge of the ways in which a protein's structure relates to its functional usefulness . . . " Guo finds only 25% of random mutations lead to substantial loss of activity. Guo extensively discusses how one of skill can take into consideration active site location, alpha helices, beta sheets, hydrophobic interactions, turns and loops, conserved sites and the like to intelligently avoid loss of activity, e.g., by substitution avoidance at key positions or with conservative amino acid substitutions. Further, Guo states that his "database can be a valuable resource for predicting the effects of mutations on protein function . . . " Substitutions to known structures are predictable and in possession the of those having the structural information. Therefore, conservative amino acid substitutions, in which one or a few amino acids in an amino acid sequence are substituted with different amino acids with highly similar properties, are also readily identified as being highly similar to a disclosed constructs, and expected to retain function. One of skill will recognize that individual substitutions, deletions, or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group.

TABLE 1

Conservative Substitution Groups

| 1 | Alanine (A) | Serine (S) | Threonine (T) | |
|---|---|---|---|---|
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Trytophan (W) | |

DETAILED DESCRIPTION

The present invention includes biosensor constructs, reprogramming methods to prepare cells useful in receiving the constructs, and assay methods employing the biosensors, e.g., to detect the presence of active agents or signals in living cells.

The biosensors generally include various complementary domain structures working together to sense a voltage or ion at a particular intracellular location, and to provide a distinct signal correlated to changes in the parameter. In a particularly useful embodiment, the biosensors are expressed in cells representative of a particular species (e.g., human), cell type of interest, or in a cell expressing a pathology of interest. Cells expressing the biosensors can be exposed to conditions or agents and monitored for signals indicating cell responses.

Biosensors Generally.

Biosensors of the present invention are generally engineered to include components specialized in providing, e.g., location, sensing, and reporting. In expression of a sensor nucleic acid construct, the peptide product can be positioned within the cell, e.g., by chaperone or transit sequences, hydrophobic affinities, or ligand/receptor interactions. The sensing domains typically change conformation in response to a changed intracellular condition or binding of a signal ion or molecule. Reporting domains typically present a detectable signal that changes in response to conformational changes in the associated sensing domain.

The intracellular location of a biosensor can optionally be controlled by a targeting domain or "tag". In some biosensors, intracellular location is generalized or passively determined. For example, the sensor may be generally dispersed throughout the nucleus and/or cytoplasm. In other cases, the function or specificity of the biosensor signal may depend on localization at a particular intracellular membrane or organelle. Examples biosensor tags include hydrophobic peptides directed to interact with membranes, ionic peptides directed to disperse in cytoplasm, chaperone sequences directing the biosensor to a particular compartment, and/or ligands directed to receptors. Tags useful in the study of intracellular signaling and in agent screening assays can include, e.g., NLS tags, lipid membrane tag, endoplasmic reticulum (ER) tags, golgi tags, endosome tags, ciliary tags, and/or the like.

Sensing domains in the biosensors change conformation in response to a changed physical condition, binding of a ligand, or change in an ionic environment. The conformational changes can, e.g., cause conformational changes in an associated reporter domain, or reposition the reporter domain to enhance or diminish the signal. Sensing domains can change conformation in response to binding of a peptide, binding of a nucleic acid, interaction with a protease, interaction with a phosphatase, changes in pH, changes in ionic strength, changes in a voltage potential, and/or the like.

Reporter domains of the biosensors can be of any appropriate type known in the art. However, in preferred embodiments, the reporters comprise one or more peptide domains, e.g., so they can be easily employed in in vivo systems. Typically the peptide reporter domain provides a specific fluorescent emission in response to a specific interrogating excitation wavelength of light. In the context of sensor domain conformational changes, FRET strategies can be effective, e.g., wherein the biosensor construct comprises paired donor/acceptor peptide pairs. In certain embodiments, the reporter domain is adapted to provide an emission in the red to near-infrared spectrum, e.g., to allow the signal to pass and be detected in three dimensions through cells or tissue layers. For example, relatively penetrating reporter emission signals can range from 500 nm to 1400 nm, 550 nm to 900 nm, 600 nm to 850 nm, 650 nm to 800 nm, or about 700 nm. In an exemplary embodiment, the reporter domain includes fluorescence enhancing amino acids, such as tryptophan, tyrosine, phenylalanine, which contribute to their intrinsic fluorescence of the domain. Optionally, the reporter domain can include regions naturally modified post-translationally to provide the desired long wavelength emissions. For example, a domain that emits in the red regions can be a modified green fluorescent protein where the fluorophore originates from an internal serine-tyrosine-glycine sequence which is modified to a 4-(p-hydroxybenzylidene)-imidazolidin-5-one structure.

Biosensor constructs can include, e.g., two, three, or four of the above described domain types, in any of a variety of functional configurations. For example, a sensor domain and reporter domain in any order can constitute a biosensor. Often, the biosensors of the invention include at least three domains, e.g., a targeting domain, a sensor domain, and a reporting domain. The three domains can be in any order, but typically the targeting domain is on one end of the construct, the sensor in the middle and the reporter on the second end. In certain configurations, the biosensor construct can be in the order (C-terminal/N-terminal or N-terminal/C-terminal) of: sensor/reporter; targeting/sensor/reporter; targeting/reporter/sensor; targeting/reporter1/sensor/reporter2 (e.g., FRET); reporter1/sensor/reporter2; sensor/reporter1/reporter2; and targeting/sensor/reporter1/reporter2.

Typically, the domains are linked together in a commonly translated construct of a single linear peptide. Optionally, the constructs can include one or more domains not in the same peptide chain as another domain. For example, separate domains may be associated in a non-covalent interaction, such as a hydrophobic interaction, a chelation, a ligand/receptor interaction, an antibody/antigen interaction, and/or the like.

In some cases, a single domain may have more than one function. For example, a sensor domain may also have a structure functioning as a targeting domain. In one embodiment, a domain may have a series of transmembrane domains, acting as both as a sensor (e.g., ligand responsive ion channel) and a membrane specific targeting domain. In another aspect, a sensor domain could also include a reporter function, e.g., acting as a donor or quencher member of a FRET pair with a separate reporter domain.

Voltage Sensing Biosensors.

Voltage sensors of the invention include many of the aspects described above, wherein the sensor domain is responsive to changes in voltage potential. For example, the voltage sensor may be sensitive to electrostatic influences in the local environment, e.g., a voltage differential across a membrane to which it is bound. Optionally the voltage sensor is sensitive to the local ionic environment. In living cells, the voltage potential is usually related to the absolute concentration of $H^+$, $Ca^{2+}$, $K^+$ and/or $Na^+$, or a concentration differential of these ions across a membrane. Therefore, voltage sensor domains typically include domains sensitive to electrostatic forces, $H^+$, $Ca^{2+}$, $K^+$ and/or $Na^+$ concentration.

Such sensors are particularly useful in association with relatively electroactive cells such as muscle cells, heart cells, and nerve cells.

Importantly, such voltage sensors can be configured to target and report the ion/voltage status specifically at intracellular locations. For example, the construct can include a targeting domain directing the construct to a cellular compartment or surface such as the nucleus, sacroplasma, plasma membrane, nerve axon, cilia, or synapse. Thus, not only can signal transduction be monitored in a cell generally, but more specific voltage differential effects can be visualized at the sub-cellular level.

Typical voltage sensitive biosensors of the invention include a transmembrane domain, voltage sensing domain, and a reporter domain. The transmembrane domain may act as a targeting domain and/or a voltage sensing domain, in some instances. In one embodiment, the voltage sensor has the domains in the order transmembrane/sensor/reporter. In preferred embodiments, the reporter is a fluorescent peptide, e.g., emitting in the red to near-infrared range.

A preferred voltage biosensor construct includes a combination of an ion channel transmembrane peptide, an ion channel voltage sensing peptide domain, and a fluorescent peptide. In an exemplary embodiment, the voltage sensor includes a modified transmembrane peptide, a modified voltage, and a fluorescent protein modified to provide red emissions. The domains of the constructs are typically configured from a combination of bioinformatics/database sequences as modified evolutionary mutagenesis.

In a particular voltage sensing domain the sequence comprises: MSSVRYEQREEPSMVNGNFGNTEEK-VEIDGDVTAPPKAAPRKSESVKKVHWNDV DQG-PNGKSEVEEEERIDIPEISGLWWGENEHGGD-DGRMEVPATWWNKLRKVISPF VMSFGFRVFGVVLIIVDFVLVIVDLSVTDKS SGAT-TAISSISLAISFFFLIDIILHIFVEG FSQYFSSKL-NIFDAAIVIVTLLVTLVYTVLDAFTDFSGATNIPRM-VNFLRTLRIIRLVR IIILVRILRLASQKTISQN (SEQ ID NO: 1). Conservative variations of the sequence would be expected to retain substantial useful function. The present voltage sensor domains include peptides comprising sequences at least 70%, 80%, 85%, 90%, 95%, 98%, or 99% identical to SEQ ID NO: 1. Function is expected to be best preserved with conservative substitutions and if the sequence retains at least 1, 2, 3, 4, 5, or all 6 of the following amino acid residues: I123, R220, R226, R229, R235, or R238. In many embodiments, preservation of R235 and I123 can be particularly useful in retaining optimal voltage sensor function.

In a particular reporter domain for the voltage sensor peptide, the sequence comprises: MVSKGEEDNMAIIKEF-MRFKVHMEGSVNGHQFKCTGEGEGRPYEAF QTAK-LKVTKGGPLPFAWDILSPQFMYGSRAFIKHPAGIPD-FFKQSFPEGFTWERVTR YEDGGVVTVMQDTSLED (SEQ ID NO: 2). Conservative variations of the sequence would be expected to retain substantial useful function. The present fluorescent reporter sensor domains include peptides comprising sequences at least 70%, 80%, 85%, 90%, 95%, 98%, or 99% identical to SEQ ID NO: 2. Preferred voltage sensing biosensors of the invention include both the voltage sensor of SEQ ID NO: 1 and the fluorescent reporter of SEQ ID NO: 2, and/or their conservative variants, as discussed above. Other fluorescent reporter domains include those that fluoresce from 500-1400 nm.

Calcium Ion Sensing Biosensors.

Calcium sensor constructs of the invention include many of the aspects described above for biosensors generally, but the sensor domain is responsive to changes in calcium ion levels. For example, the calcium sensor will typically bind $Ca^{2+}$ with a certain affinity and change conformation to some degree depending on the local $Ca^{2+}$ concentration. $Ca^{2+}$ can vary dramatically depending on cell type, and according to the influence of induced signals. For example, it can be informative to monitor muscle cells, nerve cells, cells responding to g-protein controlled signals, cells undergoing apoptosis, and/or the like. In living cells, $Ca^{2+}$ levels often vary with intracellular locations. The present calcium sensors can include targeting domains directing the sensors to any intracellular compartment of membrane, such as, e.g., a vacuole, the nucleus, cytoplasm, synapse, endoplasmic reticulum, and/or the like.

Calcium sensor domains are typically peptides homologous to portions of one or more calcium binding proteins. For example, a calcium binding domain can have a sequence similar to an evolutionary sequence found in calmodulin, calexcitin, parvalbumin, S100 proteins, calcineurin, and/or the like. All that is necessary for the sensor role is that the peptide, or peptide fragment, changes conformation with changes in calcium concentration. The change in conformation will translocate the reporter group and typically change the emission profile or intensity. Modern protein engineering techniques can be used to engineer enhancements causing the translocation of the reporter to be enhanced or quenched, e.g., by induced contact or induced conformational changes in the reporter itself.

A preferred calcium biosensor construct includes a combination of a tandem array of calcium binding domains (namely, EFhand domains) that include calmodulin and troponin motifs, and a fluorescent peptide. In an exemplary embodiment, the calcium sensor includes a modified calcium binding domain from calmodulin, troponin, and a fluorescent protein modified to provide red emissions. The domains of the constructs are typically configured from a combination of bioinformatics/database sequences as modified evolutionary mutagenesis.

In a particular calcium binding domain the sequence comprises: EFRASFNHFDRDHSGTLGPEEFKACLISLD-HMVLLTTKELGTVMRSLGQNPTEAE LQDMINEV-DADGDGTFDFPEFLTMMARKMMNDTD-SEEEGVQGTSEEEELANCF RIFDKDANGFIDEELGEILRATGEHVTEEDIEDLM- KDSDKNNGRIDFGEKLTDEEV (SEQ ID NO: 4). Conservative variations of the sequence would be expected to retain substantial useful function. The present calcium binding domains include peptides comprising sequences at least 70%, 80%, 85%, 90%, 95%, 98%, or 99% identical to SEQ ID NO: 4.

In a particular EFhand domain for the calcium sensor peptide, the sequence comprises: FKEAFSLFD-KDGDGTITTKELGTVMRSL-ELDA IIEEVDEDGS-GTIDFEEFLVMMVRQ (SEQ ID NO: 5). Conservative variations of the sequence would be expected to retain substantial useful function. The present EFhand domains include peptides comprising sequences at least 70%, 80%, 85%, 90%, 95%, 98%, or 99% identical to SEQ ID NO: 5.

In a particular reporter domain for the calcium sensor peptide, the sequence comprises: MVSKGEEDNMAIIKEF-MRFKVHMEGSVNGHQFKCTGEGEGRPYEA FQTAK-LKVTKGGPLPFAWDILSPQFMYGSRAFIKHPAGIPD-FFKQSFPEGFTWERVT RYEDGGVVTVMQDTSLED (SEQ ID NO: 6). Conservative variations of the sequence would be expected to retain substantial useful function. The present fluorescent reporter sensor domains include peptides comprising sequences at least 70%, 80%, 85%, 90%, 95%, 98%, or 99% identical to SEQ ID NO: 6.

Preferred calcium sensing biosensors of the invention include one, two, three or more of the domains identified in SEQ ID NOs: 4, 5, 6, and 7, and/or their conservative variants, as discussed above.

Biosensor Constructs in Human Cells.

The biosensors described herein can be incorporated into cells to monitor voltage and ion conditions within the cells. For example, nucleic acid constructs encoding the biosensor peptide domains can be transformed or transfected into eukaryotic cells for expression, e.g., using appropriate promoters, as is known in the art. The cells are preferably human, providing the benefit of a reliable host cell model, e.g., for study of human signal transduction and disease states. The cells are preferably stem cells or cells differentiated to a particular cell type of interest.

The nucleic acid construct can encode any biosensor described herein. For example, the construct can encode a combination of a voltage sensor domain, calcium sensor domain, targeting domain, and/or reporter domain. In one embodiment, the nucleic acid construct includes transient expression vector components directing expression of peptide chains comprising a combination of domains providing a functional biosensor. For example, the nucleic acid can express a single peptide chain comprising a combination of calcium binding domain, troponin domain, and reporter domain. In another example, the nucleic acid construct can encode a peptide comprising at least a combination of a transmembrane domain, a voltage sensing domain, and reporter domain.

In other embodiments of the nucleic acid expression constructs, an expression vector includes sequences encoding peptides of any of SEQ ID NOs: 1, 2, 3, 4, 5, 6, and/or 7. In certain embodiments functioning as voltage biosensors, the vector can include a combination of nucleic acid sequences encoding the peptides of SEQ ID NOs: 1 and 2, e.g., along with a sequence encoding a transmembrane domain, such as a G-protein domain or an ion channel domain. Such a construct can encode functional peptide sequences at least 70%, 80%, 85%, 90%, 95%, 98%, or 99% identical to the sequence of SEQ ID No: 1 and/or SEQ ID NO: 2. In preferred embodiments, the construct encodes a homologue of SEQ ID NO: 1 retaining at least the amino acids at I123, R220, R226, R229, R235, and/or R238. In many embodiments, preservation of R235 and I123 can be particularly useful in retaining optimal voltage sensor function. In other embodiments functioning as calcium sensitive biosensors, the vector can include a combination of nucleic acid sequences encoding the peptides of SEQ ID NOs: 4, 5, 6, and/or 7. Such a construct can encode functional peptide sequences at least 70%, 80%, 85%, 90%, 95%, 98%, or 99% identical to the sequence of SEQ ID No: 4, SEQ ID No: 5, SEQ ID No: 6, and/or SEQ ID NO: 7.

Useful nucleic acid constructs of the above expression vectors can include additional sequences encoding targeting tags, such as, e.g., a NLS tag, a lipid membrane tag, an ER tag, a golgi tag, an endosome tag, a mitochondrial tag, and/or a ciliary tag. For example, the targeting tag can include a sequence at least 90% identical to a sequence encoding the peptide tag sequence of SEQ ID NO: 3.

The present inventions include cells comprising the biosensors discussed herein. For example, nucleic acid constructs coding the biosensor peptides can be transduced or transfected into eukaryotic cells of choice. In preferred embodiments, the cells originate from a mammal, most preferably from a human. In many embodiments, the cell is an immortalized stem cell, or a cell fully or partially differentiated from a stem cell.

In the context of the present biosensors, cells can be initially derived from human patient samples. The advantage of such cells is that they can provide very representative responses to active agents and changed conditions for that patient. Thus, such cell models are more likely to provide information on the modes of action or efficacy of a candidate therapeutic for that patient. For example, such cell models can aid in the identification of custom tailored treatment for patients with certain disease states, such as autoimmune diseases, neurological diseases, cancer, diabetes, or pathologies from genetic flaws.

Alternately, the models can employ cells harboring a particular non-endogenous gene of interest, introduced by genetic engineering techniques. For example, the gene of interest can encode a receptor molecule, a G-protein coupled receptor, or an ion channel of interest. Typically, the host cell is a cell most representative of the cell type of interest in the research. Such model cells can be useful in providing more representative results, e.g., in monitoring a signal transduction or in screening prospective agents active in the modulation of the gene of interest.

Cellular models can be derived from inducible cells available from primary culture of cells from living animals. For example, fibroblasts or undifferentiated cells from circulating blood can be induced to provide pluripotent cells. It is notable that epigenetic processes can play a key role in directing the status of a cell to stem cell, progenitor cell, or mature cell. In Lister (Nature 471 (7336): 68-73, 2011), aberrant epigenomic programming was found capable of inducing a variety of different pluripotent stem cells (iPSCs). Female lung fibroblasts, adipose cells, and foreskin fibroblasts were reprogrammed into induced pluripotent state using OCT4, SOX2, KLF4, and MYC genes. The iPSCs were found to be similar to embryonic stem cells in many characteristics, including DNA methylation patterns. Such concepts can be used to reprogram cells, e.g., in combination with further circadian synchronization techniques, described below.

In addition to inducement by action of immortalizing genes, cell signaling was found to influence epigenetic processes governing differentiation. In the research of Baylin (e.g., Nature Biotechnology 28 (10): 1033-8, 2010), several signaling pathways were suggested as important in the induction and maintenance of embryonic stem cells and in their differentiation. For example, signaling pathways of growth factors can play a role in epigenetic regulation of cellular differentiation. These growth factors include, e.g., transforming growth factors (TGFs), fibroblast growth factors (FGFs), and bone morphogenetic proteins. Another important factor in induction and differentiation can be the Wnt signaling pathway.

Circadian rhythm influences on cellular synchronization can be employed in inducement of pluoripotential cells. For example, cells can be reprogrammed into inducible pluripotent stem cells using human clock gene and human Bmal1/2/3/4 genes and their E-box promoters. In one aspect, fibroblast iPSCs can be generated by such reprogramming, and further directed to provide inducible neurons (iN), glial cells, or inducible neural progenitor cells (iNPCs), as desired. The reprogramming factor for each cell type is typically a transcriptional regulator that is specific for the cellular lineage. Each factor can be modified to be controlled by a circadian regulatory element (such as, E-box promoters or an artificial E-box-like promoter sequence tag). Such promoter sequences can be added to each transcriptional regulator, thus forming a novel transcriptional element for control regulated by human Clock and Bmal genes.

To complement the biosensor systems described herein, induced cells can be cultured together in a "tissue" structure, e.g., in three dimensions. In this way, the cell to cell contacts of interest can be studied, e.g., using penetrating imaging available in the form of near infrared reporter signals. For example, co-cultures of iN and iG can be prepared to create a 3D model of a neuronal structure. The structure can be further controlled, e.g., using an appropriately structured scaffold, e.g., using materials not opaque to reporter signals, e.g., for confocal microscopic review.

Screening and Assay Methods Using Biosensors in Model Cells

The biosensor constructs, e.g., engineered into model cells of interest, can more predictably provide assay and screening results relevant to life science research and study of clinical pathologies of interest. That is, the present targeted biosensors in appropriate cell types, differentiated to a particular phenotype, can provide models more likely to anticipate a normal response in the modeled organism than, e.g., old art xenotypic models.

The initial steps in preparing a model system can be to identify the cell type of interest and the signal to be detected. For example, to study certain neurological disease states, one may choose to target a voltage sensor to the plasma membrane, e.g., in model cells differentiated from iPS cells. Alternately, one may elect to study a blood cell cancer using a hematopoietic blast induced to a model CML cell and signaling from a calcium sensitive biosensor construct. Typically the biosensor constructs are transiently expressed in the cells using, e.g., a CMV constitutive promoter or a cell-type-specific promoter.

Once the model system is established, the biosensor can be monitored in a single cell, or across an array of cells. For example, a cell can be exposed to a signaling agent to see if the cell type responds to that agent, e.g., a cytokine or candidate small molecule bioactive agent. Optionally, the cell can be co-transfected with a second expression construct of a peptide of interest (e.g., a tumor-associated antigen or oncogene) to monitor any influence of the external gene in a signaling pathway.

In other embodiments, the cells can be segregated into arrays complementary to low, medium, or high throughput assay formats. For example, cells can be dispensed into 96-well plates, onto a micro-well array, or a FACS sorter, for separate exposure to library members of putative candidate agents. Such arrays can be reviewed suing standard fluorescent detection equipment. Optionally, the arrays can be reviewed photographically with digital CCD based cameras. Changes in a signal, e.g., as compared to a positive or negative reference, can be flagged for additional characterization.

EXAMPLES

The following examples are offered to illustrate, but not to limit the claimed invention. The inventive concepts disclosed herein include certain biosensors sensitive to intracellular conditions, cells expressing the biosensors, and methods of monitoring the cells to detect intracellular changes, e.g., associated with an activity of an externally applied agent.

Example 1—Voltage Sensor Construct

Presented is a voltage sensor for use in intracellular environments. The voltage sensor is a peptide construct featuring a combination of interacting structural features. The expressed peptide construct includes a transmembrane domain, voltage sensing domain, and a fluorescent reporter. The transmembrane can anchor the sensor to a lipid membrane in a cell of choice. The voltage sensing domain can include, e.g., polar or ionic groups that are sensitive to changes in the surrounding ionic environment or to a voltage potential across the anchoring membrane. The fluorescent reporter is a fluorescent peptide sequence, e.g., adapted to be sensitive to conformational changes in other domains of the construct.

The transmembrane domain typically includes hydrophobic amino acid residues that interact with lipids of the membrane to anchor the construct. Further, the transmembrane domain can provide multiple transmembrane structures, together comprising an ion channel or voltage-gated channel.

The voltage sensing domain of the exemplary embodiment includes the following peptide sequence: MSSVRYEQREEPSMVNGNFGNTEEKVEIDGDVTAPPKAAPRKSESVKKVHWNDVDQGPNGKSEVEEEERIDIPEISGLWWGENEHGGDDGRME VPATWWNKLRKVISPFVMSFGFRVFGVVLIIVDFVLVIVDLSVTDKSSGATTAISSIS LAISFFFLIDIILHIFVEGFSQYFSSKLNIFDAAIVIVTLLVTLVYTVLDAFTDFSGATNI PRMVNFLRTLRIIRLVRIIILVRILRLASQKTISQN (SEQ ID NO: 1).

Structural features of note in the voltage sensing sequence include a low complexity region (amino acids 63-75), transmembrane domain (amino acids 109-131), and ion transport (amino acids 149-245). Particularly important residues in the conformational response action include I123, R220, R226, R229, R235, R238; particularly residues R235 and I123.

Conservative substitutions and variations, silent substitutions as well as variations of SEQ ID NO.: 1 which retain function are also within the scope of the invention. Such substitutions and variations include sequences more than 80% identical to SEQ ID NO.: 1, or more preferably, more than 90% identical to SEQ ID NO.: 1.

In this construct, the far-red long wavelength properties fluorophore red color intensities should be particularly sensitive to any changes in residues R235 and I123. Conformational changes in the sensing and transmembrane domains (e.g., particularly in a membrane anchored environment) lead to substantial measurable changes in the intensity (ΔF) and spectrum contours of the fluorophore domain emissions.

The following is an example of a useful fluorescent-red reporter domain sequence: MVSKGEEDNMAIIKEFMRFKVHMEGSVNGHQFKCTGEGEGRPYEAFQ TAKLKVTKGGPLPFAWDILSPQFMYGSRAFIKHPAGIPDFFKQSFPEGFTWERVTRY EDGGVVTVMQDTSLED (SEQ ID NO: 2). Conservative substitutions and variations, silent substitutions as well as variations of SEQ ID NO.: 2 which retain function are also within the scope of the invention. Such substitutions and variations include sequences more than 80% identical to SEQ ID NO.: 2, or more preferably, more than 90% identical to SEQ ID NO.: 2. A useful fluorescent reporter domain sequence includes any sequence which fluoresces in the range from 500 to 1400 nm.

Example 2—Calcium Sensor Construct

The structural features of exemplary calcium sensor constructs include a complementary combination of a calmodulin-binding domain, a troponin domain, and a fluorescent reporter domain. The construct can further include one or more tag sequences to target the construct to a particular intracellular location or environment. The complementary combination of tandem arrays of EF-hand domains that include a calmodulin-like-binding domain and a troponin-like domain, and a fluorescent reporter domain. The fluorescent reporter is a fluorescent peptide sequence, e.g., adapted to be sensitive to conformational changes in other domains of the construct.

The calcium sensor components interact as follows. Calcium-binding to EF hand domains leads to a conformational change and surface hydrophobicity changes in the peptide construct. The changed calcium binding domains then interact differently with the fluorescent reporter domain causing a substantial and measurable change in the intensity of the fluorophore (ΔF) emissions.

The calcium sensing domains of the exemplary embodiment includes the following peptide sequence:

```
                                         (SEQ ID NO: 12)
MVDSSRRKWNKAGHAVRAIGRLSSPVVSERMYPEDGALKSEIKK

GLRLKDGGHYAAEVKTTYKAKKPVQLPGAYIVDIKLDIVSHNEDY

TIVEQCERAEGRHSTGGMDELYKGGTGGSLVSKGEENNMAVIKA

EFMRFKEHMEAGSVNGHEFEIAEGEGEGRPYEAGTQTARLKVTKG

GPLPFAWDAILSPQIMYGSAKAYVKHPADIAPDYLKLSFPEAGFK

WERVMNFEDGGVVHVNQADSSLQDGVFIAYKVKLRGTNFAPPDG

PVMQKKATMGWEATRDQLTEEEFRASFNHFDRDHSGTLGPEEFK

ACLISLDHMVLLTTKELGTVMRSLGQNPTEAELQDMINEVDADGD

GTFDFPEFLTMMARKMMNDTDSEEEGVQGTSEEEELANCFRIFDK

DANGFIDEELGEILRATGEHVTEEDIEDLMKDSDKNNGRIDFGEKL

TDEEVFKEAFSLFDKDGDGTITTKELGTVMRSLELDAIIEEVDEDGS

GTIDFEEFLVMMVRQGQNPTKEEELANCFRIFDKNADGFIDIEELG

EILRAT.
```

The red fluorescent indicator can include the following far-red reporter domain sequence:

```
                                         (SEQ ID NO: 6)
MVSKGEEDNMAIIKEFMRFKVHMEGSVNGHQFKCTGEGEGRPYEAFQTAK

LKVTKGGPLPFAWDILSPQFMYGSRAFIKHPAGIPDFFKQSFPEGFTWER

VTRYEDGGVVTVMQDTSLED.
```

Example 3—Targeting Tags

In many cases, it is advantageous to direct the voltage sensor or calcium sensor to a particular intracellular membrane or compartment. The biosensors of the invention can include peptide segments adapted to have an affinity for a cellular target.

Exemplary peptide sequences useful in targeting biosensors to a desired intracellular location include, e.g.:
NLS tag (protein sequence): DPKKKRKV (SEQ ID NO: 3).
ER tag: KDEL (SEQ ID NO: 8)
Endosome tag: NPTY-DXXLL-YXXoo (protein sequence; tandem motifs; oo=2 two residues with hydrophobic side groups (SEQ ID NO: 9);
Ciliary tag: VxPx-RVxP-KVHPSST-AxEGG (protein sequence; tandem motifs—SEQ ID NO: 10)
Human endosome sequence tag MTSRKKVLLKVIILGDSGVGKTSLMHRYVND (SEQ ID NO: 11)
SEQ ID NO: 16 human synapsin tag:

```
CCTGCAGGGCCCACTAGTATCTGCAGAGGGCCCTGCGTATGAG

TGCAAGTGGGTTTTAGGACCAGGATGAGGCGGGGTGGGGGTGC

CTACCTGACGACCGACCCCGACCCACTGGACAAGCACCCAACC

CCCATTCCCCAAATTGCGCATCCCCTATCAGAGAGGGGAGGG

GAAACAGGATGCGGCGAGGCGCGTGCGCACTGCCAGCTTCAGC

ACCGCGGACAGTGCCTTCGCCCCCGCCTGGCGGCGCGCGCCAC

CGCCGCCTCAGCACTGAAGGCGCGCTGACGTCACTCGCCGGTC

CCCCGCAAACTCCCCTTCCCGGCCACCTTGGTCGCGTCCGCGCC

GCCGCCGGCCCAGCCGGACCGCACCACGCGAGGCGCGAGATAG

GGGGGCACGGGCGCGACCATCTGCGCTGCGGCGCCGGCGACTC

AGCGCTGCCTCAGTCTGCGGTGGGCAGCGGAGGAGTCGTGTCG

TGCCTGAGAGCGCAGCTGTGCTCCTGGGCACCGCGCAGTCCGC

CCCCGCGGCTCCTGGCCAGACCACCCCTAGGACCCCCTGCCCCA

AGTCGCAGCC
```

SEQ ID NO: 17 Human synaptic vesicle tag:

```
MDCLCIVTTK KYRYQDEDTP PLEHSPAHLP NQANSPPVIV

NTDT LEAPGYELQVNGTEGE MEYEEITLER GNSGLGESIA

GGTDNPHIGD DPSIFITKIIPGGAAAQDGR LRVNDSILEV

NEVDVREVPH SAAVEALKEA GSIVRLYVMRRKPPAEKVME

IKLIKGPKGL GFSIAGGVGN STSLEITASM
```

TempoEndo protein seq; TempoVol with Endosome tag (SEQ ID NO: 13)
MTSRKKVLLKVIILGDSGVGKTSLMHRYVNDMSSVRYEQREEPS

MVNGNFGNTEEKVEIDGDVTAPPKAAPRKSESVKKVHWNDVDQ

GPNGKSEVRNEERIDIPEISALWWGENEHGADDGRMELPATMWN

KLRKVISPFVMSFGFRVFGVVLIIVDFVLVIVDLSVTDKSSNATTAI

ESISLAISFFFLIDIILRIFVEGFNQYFSSKLNIFDAAIVIVTLLVTLVY

TVLDAFTDFSGATNIPRMVNFLRTLRIIRLVRIFRLASQKRELRLASR

RTISQN.

Tags are (in most cases) N-terminal for each sensor-reporter construct.

Example 4—Methods of Reprogramming Cells

Human fibroblasts can be reprogrammed to a pluripotent state. Such cells can then be differentiated to a degree to provide cell type specific model systems for expression of the biosensors.

Fibroblast cells are reprogrammed into inducible pluripotent stem cells (iPSC) over the course of ~10 days, using a circadian rhythm (cellular synchronization) induced method in combination with transcriptional regulatory control modification. For example, human clock gene and human Bmal1/2/3/4 genes can be employed, e.g., using associated E-box promoters.

Each reprogramming factor is typically a transcriptional regulator that is specific for the cellular lineage and each factor is modified to be controlled by a circadian regulatory element (E-box promoters or an artificial E-box-like promoter sequence tag). The promoter sequences are added to each transcriptional regulator, thus forming a novel transcriptional element and control, regulated by human Clock and Bmal genes.

Fibroblast cells can be reprogrammed into inducible neurons (iN), glial cells (astrocytes included, iG), and inducible neural progenitor cells (iNPCs) using a similar approach as the iPSC but with specific transcription factors suitable for their lineages.

Co-cultures of iN and iG are performed to create a 3D model, using a proprietary in vitro scaffold.

Example 5—Methods for Screening Reprogrammed Cells

The sensors described herein can be introduced into reprogrammed cells, e.g., to monitor interactions of signaling moieties intracellularly. Further, the reprogrammed cells can be exposed to candidate agent molecules to monitor the effects of the agents on intracellular calcium levels and/or voltage potential of the cells.

Nucleic acids encoding the biosensors can be transiently (48 hrs) transduced into selected cells for expression, e.g., using standard electroporation techniques. Further genetic modifications can be performed on the cells to express genes-of-interest (a GPCR, channel, receptor, etc). Such cells can act as representative models for study of signaling interactions and bioactive agents.

In one option, cells are initially directly derived from patient samples. After reprogramming and introduction of biosensors, such cells can provide model systems and assay results more likely to reflect patient responses. In the patient derived cell context, e.g., patient fibroblasts can be rendered pluripotent, differentiated to the extent desired to reflect, e.g., a target cell of a pathology. Depending on the pathology of interest, a biosensor is adapted to be targeted to a location of interest, to detect relevant voltage or calcium levels, and provide a signal appropriate to the detection system in use.

In another option, an external (e.g., non-endogenous) gene of interest is introduced to the cells for study. For example, a gene of interest, such as a receptor molecule, GPCR, or a channel, can be molecularly cloned from a human cDNA library before the gene and transfected into the cells. A biosensor is also introduced to the cells, and a cellular functional assay is performed. In this way, encoded peptides of the gene can be studies in the unique environment of relevant cells. Such model cells (e.g., reprogrammed human cells expressing abnormal receptors) can provide biosensor signals more likely to reflect associated live animal results than other in vitro assays.

The following is a typical experimental design. Cells of interest are seeded into a multi-well format (12, 24, 48, 96, 384, or 1538-well formats). Sensor expression constructs are introduced using standard transfection procedures. 36-48 hours post transfection, cellular functional assays may begin, after correctly assessing the expression levels of the sensors. Stimuli for each experiment depends on the nature of the receptor or channel being assayed and what are the relevant phenotypic/disease conditions applied. If an agent of interest (e.g., a particular molecule or ligand) is known, it is dissolved in liquid solution to be applied to the cells.

A baseline can be established before application of the agent. Typically excitation wavelengths are set to ~450-570 nm. Emission wavelengths typically range ~500-700 nm. Fluorescence is sampled every ~3 seconds at an exposure time ~500 ms. ΔF/F is calculated by subtracting the baseline fluorescence level (e.g., 20 data points), subtracted from the actual fluorescence response and normalized to the starting fluorescence value. The percent fluorescence change is calculated for each region of interest in a cell or tissue using scripts in ImageJ, Matlab or any proprietary softwares developed by manufacturers (such as Molecular Devices, Tecan, BioTek, etc.) software algorithms.

Example 6—Screening and Discovery Using Human Cellular Models

It is envisioned that the biosensors and model cell systems described herein can be used in any number of formats and contexts to monitor intercellular interactions, signal transduction, and intracellular responses. For example, the following utilities can be realized.

1) Human iPSCs-derived can be employed to cell types to generate 2D or 3D cellular models of human disease models and using biosensors to screen for chemical, biologics, drug-like, and toxicology compounds, e.g., to identify and evaluate candidate drug compounds.

2) A synthesized and genetically encoded biosensor can be prepared to function as a reporter of $Ca^{2+}$ concentrations in human cells, e.g., resolving events in cellular compartments such as the nucleus, cytoplasm, plasma membrane, and/or the like.

3) A synthesized and genetically encoded biosensor can function as a reporter of cellular voltage changes in human cells, e.g., in compartments such as the nucleus, cytoplasm, or plasma membrane. Voltage sensors could evaluate and report fluctuations in membrane potentials due to changes in sodium ($Na^+$) and potassium ($K^+$) concentrations.

4) Biosensors can be used in a cell-type specific manner. For example, based on the disclosures herein, one can genetically modify a biosensor to contain specific promoter sequences for cell types, e.g., dopaminergic neurons, GABAergic neurons, astrocytes, cardiomyocytes, HSCs, NPCs, MSCs, cancer cells, cancer stem cells, and/or the like. Human and mammalian cell types are generally of particular importance and interest.

5) Biosensors signaling in long wavelength ranges (e.g., 500 nm-750 nm range) can be used to detect interactions through three dimensions of a biologic sample.

6) Using biosensors with sequence identities with at least 70% identity to the following sequences (to be shown soon).

7) Using human cellular models conveniently derived from fibroblast or blood to provide information specific to a patient or cell type.

8) Reprogramming Parkinson patient-derived inducible pluripotent cells (iPSCs) from blood or fibroblast biopsies are into neural progenitor cells (NPCs). Appropriate biosensors are introduced to the cells using electroporation or chemical transfection methods (standard). Plate cells into multi-well plates (24, 48, 95, or 1500-well plates). Apply compounds to the cells via standard loading methods. Fluorescence excitation begins the experiment. Stimulation solutions are followed by washing solutions. Measurements are taken and changes in fluorescence ($\Delta F$) and ratio ($\Delta F/F$) are calculated and plotted against time (milli-seconds to seconds timeframe). Alternatively, to calculate using a single intensiometric reporter would require standardization of the baseline responses and calculation of the changes in fluorescent intensities in response to a chemical or biological compound.

9) Rett syndrome patient-derived inducible pluripotent cells (iPSCs) from blood or fibroblast biopsies are induced into primary neurons, astrocytes and co-cultures of neuronastrocytes from affected-patients and unaffected individuals. Biosensors are introduced to the cells using electroporation or chemical transfection methods (standard). Cells are plated into multi-well plates (24, 48, 95, or 1500-well plates). Compounds are applied to the cells via standard loading methods. Fluorescence excitation begins the experiment. Stimulation solutions are followed by washing solutions. Measurements are taken and changes in fluorescence ($\Delta F$) and ratio ($\Delta F/F$) are calculated and plotted against time (milli-seconds to seconds timeframe). Alternatively, to calculate using a single intensiometric reporter would require standardization of the baseline responses and calculation of the changes in fluorescent intensities in response to a chemical or biological compound.

10) An early-to-mid-stage biopharmaceutical company looking for a new method of screening their library of compounds (specifically, biologics and synthesized peptides) requires a new screening method. Progenitor cells (NPCs, MSCs, HSCs) are generated and voltage-biosensors are introduced to the cells. Then, cells are plated into multi-well plates (24, 48, 95, or 1500-well plates). Compounds are applied to the cells via standard loading methods. Fluorescence excitation begins the experiment. Stimulation solutions are followed by washing solutions. Measurements are taken and changes in fluorescence ($\Delta F$) and ratio ($\Delta F/F$) are calculated and plotted against time (milli-seconds to seconds timeframe). Alternatively, to calculate using a single intensiometric reporter would require standardization of the baseline responses and calculation of the changes in fluorescent intensities in response to a chemical or biological compound.

11) A company wishes to adopt a new toxicology technology to evaluate the effects of their candidate compounds in a physiologically relevant cellular environment, e.g., using human primary/derived/induced cell types and co-cultures in a 2D or 3D model. Equipment would include a multi-plate fluorescent reader (example: TECAN's M1000Pro) or a high-content cellular imager (GE's IN Cell 6000).

12) A company wishes to screen a drug candidate against a population of patients' derived cells (personalized medicine indications), in order to determine the most appropriate genotypes for the candidate compound (for clinical phase 1/2/3 studies and evaluation). The company could be offered two sets of custom-services—first, to make progenitor cell types (NPCs, HPCs, or MSCs) and introduce biosensors for screening; second, to make specific cell types (neurons, glial, cardiomyocytes, liver, etc) and introduce biosensors for screening.

Example 7-2D Versus 3D Human Cellular Models

Traditionally, cell culture models in 2D are performed as monolayers. Culturing human cells in 3D requires specialized cell culture dishes with coating (e.g., Lipidure® coating or Nunc®) and sometimes, U-shaped, V-shaped, or F-shaped dish bottoms. Recently, numerous studies in human cancer and stem cell fields have pointed to the importance of 3D culture. 3D cultures allow cancer cells to form tumors as spheroids (see Figure 21. Many in the academic literature have suggested that the 3D spheroids are more predictive of cancer cellular responses to drug compounds. Thus, using 3D spheroid models provide a new and improved model to predict tumor responses to a chemical compound (aka. chemical compound in a drug library).

Example 8—ATP Biosensor

ATP-turnover in the mammalian cell types is a reflection of mitochondrial activity. Mitochondria are metabolic energy generators/organelles in the cell. ATP is a byproduct of the cellular metabolic process. Thus, a reporter of ATP levels in a LIVE-cell assay is a reporter of mitochondrial activity and metabolic functions, and may be indicative of dysfunctions due to disease states due to human mutations or polymorphisms, signal transduction pathway disruptions, or mitochondrial dysfunction. The ATP biosensor of the invention includes a domain that senses and binds to ATP (which may target ATP in the cytosol or in mitochondria) and a domain that is a fluorescent reporter in the 500 to 1400 nm (excitation/emission) range, with the preferred ranges in the 500 to 600 (excitation/emission) range. Cytosolic measurements of ATP can determine the effects of internal or external factors on cytotoxicity in most cases, although targeting measurements to the mitochondrial inner membrane can be useful under special circumstances.

ATP-Binding Biosensor, TempoATP:

```
                                        (SEQ ID NO: 14)
MDYKDDDDKKTNWQKRIYRVKPCVICKVAPRDWWVENRHLRIY

TMCKTCFSNCINYGDDTYYGHDDWLMYTDCKEFSNTYHNLGRLP

DEDRHWSASCHHHHHHMGMSGSMVSKGEELIKENMRMKVVME

GSVNGHQFKCTGEGEGNPYMGTQTMRIKVIEGGPLPFAFDILATSF

MYGSRTFIKYPKGIPDFIKQSFPEGFTWERVTRYEDGGVVTVMQD
```

-continued

TSLEDGCLVYHVQVRGVNFPSNGPVMQKKTKGWEPNTEMMYPA

DGGLRGYTHMALKVDGGGHLSCSFVTTYRSKKTVGNIKMPGIHA

VDHRLERLEESDNEMFVVQREHAVAKFAGLGGGMDELYK.

Conservative substitutions and variations, silent substitutions as well as variations of SEQ ID NO.: 14 which retain function are also within the scope of the invention. Such substitutions and variations include sequences more than 80% identical to SEQ ID NO.: 14, or more preferably, more than 90% identical to SEQ ID NO.: 14.

In SEQ ID NO: 14, the first portion thereof is the ATP-binding portion, i.e.:

(SEQ ID NO: 18)
MDYKDDDDKKTNWQKRIYRVKPCVICKVAPRDWWVENRHLRIYTMCKTC

FSNCINYGDDTYYGHDDWLMYTDCKEFSNTYHNLGRLPDEDRHWSASCHH

HHHHMGMSGS.

Conservative substitutions and variations, silent substitutions as well as variations of SEQ ID NO.: 18 which retain function are also within the scope of the invention. Such substitutions and variations include sequences more than 80% identical to SEQ ID NO.: 18, or more preferably, more than 90% identical to SEQ ID NO.: 18.

In SEQ ID NO: 14, the latter portion thereof is the reporter portion which fluoresces in the red range, i.e.:

(SEQ ID NO: 19)
MVSKGEELIKENMRMKVVMEGSVNGHQFKCTGEGEGNPYMGTQ

TMRIKVIEGGPLPFAFDILATSFMYGSRTFIKYPKGIPDFFKQSFPEG

FTWERVTRYEDGGVVTVMQDTSLEDGCLVYHVQVRGVNFPSNGP

VMQKKTKGWEPNTEMMYPADGGLRGYTHMALKVDGGGHLSCS

FVTTYRSKKTVGNIKMPGIHAVDHRLERLEESDNEMFVVQREHAV

AKFAGLGGGMDELYK.

Conservative substitutions and variations, silent substitutions as well as variations of SEQ ID NO.: 19 which retain function are also within the scope of the invention. Such substitutions and variations include sequences more than 80% identical to SEQ ID NO.: 19, or more preferably, more than 90% identical to SEQ ID NO.: 19.

Example 9—Heme Biosensor

Tempo's Heme biosensor includes a domain that senses and binds to heme (amino acid residues 1-205) and a domain that is a fluorescent reporter in the 605 nm to 635 nm (excitation/emission) range.

Oxygen-Heme-Binding Biosensor, TempoHEME (SEQ ID NO: 15)
MAAMLEPEPVVAEGTAAQAVETPDWEAPEDAGAQPGSYEIRHYG

PAKWVSTCVESMDWDSAVQTGFTKLNSYIQGKNEKGMKIKMTAP

VLSYVEPGPGPFSESTITISLYIPSEQQSDPPRPSESDVFIEDRAKMTV

FARCFEGFCSAQKNQEQLLTLASILREEGKVFDEKVFYTAGYNSPF

RLLDKNNEVWLIQKNKPFKANEMVSKGEELIKENMRMKVVMEGS

VNGHQFKCTGEGEGNPYMGTQTMRIKVIEGGPLPFAFDILATSFM

YGSRTFIKYPKGIPDFFKQSFPEGFTWERVTRYEDGGVVTVMQDTS

LEDGCLVYHVQVRGVNFPSNGPVMQKKTKGWEPNTEMMYPADG

GLRGYTHMALKVDGGGHLSCSFVTTYRSKKTVGNIKMPGIHAVD

HRLERLEESDNEMFVVQREHAVAKFAGLGGGMDELYK.

Conservative substitutions and variations, silent substitutions as well as variations of SEQ ID NO.: 15 which retain function are also within the scope of the invention. Such substitutions and variations include sequences more than 80% identical to SEQ ID NO.: 15, or more preferably, more than 90% identical to SEQ ID NO.: 15.

It is understood that the examples and embodiments described herein are for illustrative purposes only and that various modifications or changes whether or not suggested to persons skilled in the art and are to be included within the scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A nucleic acid construct encoding an oxygen sensor peptide construct comprising: a heme-binding domain comprising the sequence of SEQ ID NO: 15 and a fluorescent reporter domain, wherein the fluorescent reporter is adapted to fluoresce at wavelength in the range from 500 nm to 1400 nm, and wherein the fluorescent reporter domain is adapted to change fluorescent emissions characteristics in response to binding of the heme-binding domain to heme.

2. A cell transformed with the nucleic acid construct of claim 1.

3. The cell of claim 2 which is a human cell.

4. The cell of claim 2 which is an iPSC derived cell, or is derived from a fibroblast or a blood cell.

5. A vector including the construct of claim 1.

6. A process of making a cell transformed with the nucleic acid construct of claim 1, comprising:
    transfecting the nucleic acid construct of claim 1 into a eukaryotic cell; and
    expressing the transfected nucleic acid construct by the cell.

7. The process of claim 6 wherein the cell is a human cell.

8. The process of claim 6 wherein the cell is an iPSC derived cell, or is derived from a fibroblast or a blood cell.

9. A process of making a cell acting as a heme biosensor, comprising: transforming the cell with a nucleic acid construct of claim 1.

10. The process of claim 9 wherein the fluorescent reporter sequence is at least 80% identical to the sequence of SEQ ID NO: 2.

11. The process of claim 9 wherein the fluorescent reporter sequence is at least 90% identical to the sequence of SEQ ID NO: 2.

12. The process of claim 9 wherein the cell is a human cell.

13. The process of claim 9 wherein the cell is an iPSC derived cell, or is derived from a fibroblast or a blood cell.

* * * * *

SEQUENCE LISTING

```
<160> NUMBER OF SEQ ID NOS: 19

<210> SEQ ID NO 1
<211> LENGTH: 248
<212> TYPE: PRT
<213> ORGANISM: Artificial
<220> FEATURE:
<223> OTHER INFORMATION: recombinant voltage sensing domain

<400> SEQUENCE: 1

Met Ser Ser Val Arg Tyr Glu Gln Arg Glu Glu Pro Ser Met Val Asn
1               5                   10                  15

Gly Asn Phe Gly Asn Thr Glu Glu Lys Val Glu Ile Asp Gly Asp Val
```

```
                    20                  25                  30
Thr Ala Pro Pro Lys Ala Ala Pro Arg Lys Ser Glu Ser Val Lys Lys
                35                  40                  45
Val His Trp Asn Asp Val Asp Gln Gly Pro Asn Gly Lys Ser Glu Val
 50                  55                  60
Glu Glu Glu Arg Ile Asp Ile Pro Glu Ile Ser Gly Leu Trp Trp
 65                  70                  75                  80
Gly Glu Asn Glu His Gly Gly Asp Asp Gly Arg Met Glu Val Pro Ala
                85                  90                  95
Thr Trp Trp Asn Lys Leu Arg Lys Val Ile Ser Pro Phe Val Met Ser
               100                 105                 110
Phe Gly Phe Arg Val Phe Gly Val Val Leu Ile Ile Val Asp Phe Val
               115                 120                 125
Leu Val Ile Val Asp Leu Ser Val Thr Asp Lys Ser Ser Gly Ala Thr
           130                 135                 140
Thr Ala Ile Ser Ser Ile Ser Leu Ala Ile Ser Phe Phe Leu Ile
145                 150                 155                 160
Asp Ile Ile Leu His Ile Phe Val Glu Gly Phe Ser Gln Tyr Phe Ser
               165                 170                 175
Ser Lys Leu Asn Ile Phe Asp Ala Ala Ile Val Ile Val Thr Leu Leu
               180                 185                 190
Val Thr Leu Val Tyr Thr Val Leu Asp Ala Phe Thr Asp Phe Ser Gly
               195                 200                 205
Ala Thr Asn Ile Pro Arg Met Val Asn Phe Leu Arg Thr Leu Arg Ile
           210                 215                 220
Ile Arg Leu Val Arg Ile Ile Leu Val Arg Ile Leu Arg Leu Ala
225                 230                 235                 240
Ser Gln Lys Thr Ile Ser Gln Asn
               245

<210> SEQ ID NO 2
<211> LENGTH: 120
<212> TYPE: PRT
<213> ORGANISM: Artificial
<220> FEATURE:
<223> OTHER INFORMATION: recombinant fluorescent reporter domain

<400> SEQUENCE: 2

Met Val Ser Lys Gly Glu Glu Asp Asn Met Ala Ile Ile Lys Glu Phe
 1               5                  10                  15
Met Arg Phe Lys Val His Met Glu Gly Ser Val Asn Gly His Gln Phe
               20                  25                  30
Lys Cys Thr Gly Glu Gly Glu Gly Arg Pro Tyr Glu Ala Phe Gln Thr
           35                  40                  45
Ala Lys Leu Lys Val Thr Lys Gly Gly Pro Leu Pro Phe Ala Trp Asp
 50                  55                  60
Ile Leu Ser Pro Gln Phe Met Tyr Gly Ser Arg Ala Phe Ile Lys His
 65                  70                  75                  80
Pro Ala Gly Ile Pro Asp Phe Phe Lys Gln Ser Phe Pro Glu Gly Phe
               85                  90                  95
Thr Trp Glu Arg Val Thr Arg Tyr Glu Asp Gly Gly Val Val Thr Val
               100                 105                 110
Met Gln Asp Thr Ser Leu Glu Asp
           115                 120
```

```
<210> SEQ ID NO 3
<211> LENGTH: 8
<212> TYPE: PRT
<213> ORGANISM: Artificial
<220> FEATURE:
<223> OTHER INFORMATION: polypeptide tag for nuclear localization

<400> SEQUENCE: 3

Asp Pro Lys Lys Lys Arg Lys Val
1               5

<210> SEQ ID NO 4
<211> LENGTH: 164
<212> TYPE: PRT
<213> ORGANISM: Artificial
<220> FEATURE:
<223> OTHER INFORMATION: recombinant calcium binding domain

<400> SEQUENCE: 4

Glu Phe Arg Ala Ser Phe Asn His Phe Asp Arg Asp His Ser Gly Thr
1               5                   10                  15

Leu Gly Pro Glu Glu Phe Lys Ala Cys Leu Ile Ser Leu Asp His Met
                20                  25                  30

Val Leu Leu Thr Thr Lys Glu Leu Gly Thr Val Met Arg Ser Leu Gly
            35                  40                  45

Gln Asn Pro Thr Glu Ala Glu Leu Gln Asp Met Ile Asn Glu Val Asp
50                  55                  60

Ala Asp Gly Asp Gly Thr Phe Asp Phe Pro Glu Phe Leu Thr Met Met
65                  70                  75                  80

Ala Arg Lys Met Met Asn Asp Thr Asp Ser Glu Glu Glu Gly Val Gln
                85                  90                  95

Gly Thr Ser Glu Glu Glu Leu Ala Asn Cys Phe Arg Ile Phe Asp
            100                 105                 110

Lys Asp Ala Asn Gly Phe Ile Asp Glu Glu Leu Gly Glu Ile Leu Arg
        115                 120                 125

Ala Thr Gly Glu His Val Thr Glu Glu Asp Ile Glu Asp Leu Met Lys
130                 135                 140

Asp Ser Asp Lys Asn Asn Gly Arg Ile Asp Phe Gly Glu Lys Leu Thr
145                 150                 155                 160

Asp Glu Glu Val

<210> SEQ ID NO 5
<211> LENGTH: 57
<212> TYPE: PRT
<213> ORGANISM: Artificial
<220> FEATURE:
<223> OTHER INFORMATION: recombinant EF hand binding domain

<400> SEQUENCE: 5

Phe Lys Glu Ala Phe Ser Leu Phe Asp Lys Asp Gly Asp Gly Thr Ile
1               5                   10                  15

Thr Thr Lys Glu Leu Gly Thr Val Met Arg Ser Leu Glu Leu Asp Ala
                20                  25                  30

Ile Ile Glu Glu Val Asp Glu Asp Gly Ser Gly Thr Ile Asp Phe Glu
            35                  40                  45

Glu Phe Leu Val Met Met Val Arg Gln
        50                  55

<210> SEQ ID NO 6
<211> LENGTH: 120
```

```
<212> TYPE: PRT
<213> ORGANISM: Artificial
<220> FEATURE:
<223> OTHER INFORMATION: recombinant fluorescent reporter domain

<400> SEQUENCE: 6

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Gln Phe
            20                  25                  30

Lys Cys Thr Gly Glu Gly Glu Gly Arg Pro Tyr Glu Ala Phe Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Arg Ala Phe Ile Lys His
65                  70                  75                  80

Pro Ala Gly Ile Pro Asp Phe Phe Lys Gln Ser Phe Pro Glu Gly Phe
                85                  90                  95

Thr Trp Glu Arg Val Thr Arg Tyr Glu Asp Gly Gly Val Val Thr Val
            100                 105                 110

Met Gln Asp Thr Ser Leu Glu Asp
            115                 120

<210> SEQ ID NO 7
<211> LENGTH: 258
<212> TYPE: PRT
<213> ORGANISM: Artificial
<220> FEATURE:
<223> OTHER INFORMATION: recombinant calcium binding and EF hand domains

<400> SEQUENCE: 7

Glu Phe Arg Ala Ser Phe Asn His Phe Asp Arg Asp His Ser Gly Thr
1               5                   10                  15

Leu Gly Pro Glu Glu Phe Lys Ala Cys Leu Ile Ser Leu Asp His Met
            20                  25                  30

Val Leu Leu Thr Thr Lys Glu Leu Gly Thr Val Met Arg Ser Leu Gly
        35                  40                  45

Gln Asn Pro Thr Glu Ala Glu Leu Gln Asp Met Ile Asn Glu Val Asp
    50                  55                  60

Ala Asp Gly Asp Gly Thr Phe Asp Phe Pro Glu Phe Leu Thr Met Met
65                  70                  75                  80

Ala Arg Lys Met Met Asn Asp Thr Asp Ser Glu Glu Glu Gly Val Gln
                85                  90                  95

Gly Thr Ser Glu Glu Glu Leu Ala Asn Cys Phe Arg Ile Phe Asp Lys
            100                 105                 110

Lys Asp Ala Asn Gly Phe Ile Asp Glu Glu Leu Gly Glu Ile Leu Arg
            115                 120             125

Ala Thr Gly Glu His Val Thr Glu Glu Asp Ile Glu Asp Leu Met Lys
    130                 135                 140

Asp Ser Asp Lys Asn Asn Gly Arg Ile Asp Phe Gly Glu Lys Leu Thr
145                 150                 155                 160

Asp Glu Glu Val Phe Lys Glu Ala Phe Ser Leu Phe Asp Lys Asp Gly
                165                 170                 175

Asp Gly Thr Ile Thr Thr Lys Glu Leu Gly Thr Val Met Arg Ser Leu
            180                 185                 190

Glu Leu Asp Ala Ile Ile Glu Glu Val Asp Glu Asp Gly Ser Gly Thr
            195                 200                 205
```

```
Ile Asp Phe Glu Glu Phe Leu Val Met Met Val Arg Gln Gly Gln Asn
        210                 215                 220

Pro Thr Lys Glu Glu Glu Leu Ala Asn Cys Phe Arg Ile Phe Asp Lys
225                 230                 235                 240

Asn Ala Asp Gly Phe Ile Asp Ile Glu Glu Leu Gly Glu Ile Leu Arg
                245                 250                 255

Ala Thr

<210> SEQ ID NO 8
<211> LENGTH: 4
<212> TYPE: PRT
<213> ORGANISM: Artificial
<220> FEATURE:
<223> OTHER INFORMATION: polypeptide tag for ER localization

<400> SEQUENCE: 8

Lys Asp Glu Leu
1

<210> SEQ ID NO 9
<211> LENGTH: 14
<212> TYPE: PRT
<213> ORGANISM: Artificial
<220> FEATURE:
<223> OTHER INFORMATION: polypeptide tag for endosomal localization
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa is an amino acid with a hydrophobic side
      chain

<400> SEQUENCE: 9

Asn Pro Thr Tyr Asp Xaa Xaa Leu Leu Tyr Xaa Xaa Xaa Xaa
1               5                   10

<210> SEQ ID NO 10
<211> LENGTH: 20
<212> TYPE: PRT
<213> ORGANISM: Artificial
<220> FEATURE:
<223> OTHER INFORMATION: polypeptide tag for ciliary localization
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 10

Val Xaa Pro Xaa Arg Val Xaa Pro Lys Val His Pro Ser Ser Thr Ala
1               5                   10                  15
```

```
Xaa Glu Gly Gly
         20

<210> SEQ ID NO 11
<211> LENGTH: 31
<212> TYPE: PRT
<213> ORGANISM: Homo sapiens

<400> SEQUENCE: 11

Met Thr Ser Arg Lys Lys Val Leu Leu Lys Val Ile Ile Leu Gly Asp
1               5                   10                  15

Ser Gly Val Gly Lys Thr Ser Leu Met His Arg Tyr Val Asn Asp
            20                  25                  30

<210> SEQ ID NO 12
<211> LENGTH: 546
<212> TYPE: PRT
<213> ORGANISM: Artificial
<220> FEATURE:
<223> OTHER INFORMATION: recombinant calcium binding domain

<400> SEQUENCE: 12

Met Val Asp Ser Ser Arg Arg Lys Trp Asn Lys Ala Gly His Ala Val
1               5                   10                  15

Arg Ala Ile Gly Arg Leu Ser Ser Pro Val Val Ser Glu Arg Met Tyr
            20                  25                  30

Pro Glu Asp Gly Ala Leu Lys Ser Glu Ile Lys Lys Gly Leu Arg Leu
        35                  40                  45

Lys Asp Gly Gly His Tyr Ala Ala Glu Val Lys Thr Thr Tyr Lys Ala
50                  55                  60

Lys Lys Pro Val Gln Leu Pro Gly Ala Tyr Ile Val Asp Ile Lys Leu
65                  70                  75                  80

Asp Ile Val Ser His Asn Glu Asp Tyr Thr Ile Val Glu Gln Cys Glu
                85                  90                  95

Arg Ala Glu Gly Arg His Ser Thr Gly Gly Met Asp Glu Leu Tyr Lys
            100                 105                 110

Gly Gly Thr Gly Gly Ser Leu Val Ser Lys Gly Glu Glu Asn Asn Met
        115                 120                 125

Ala Val Ile Lys Ala Glu Phe Met Arg Phe Lys Glu His Met Glu Ala
130                 135                 140

Gly Ser Val Asn Gly His Glu Phe Glu Ile Ala Glu Gly Glu Gly Glu
145                 150                 155                 160

Gly Arg Pro Tyr Glu Ala Gly Thr Gln Thr Ala Arg Leu Lys Val Thr
                165                 170                 175

Lys Gly Gly Pro Leu Pro Phe Ala Trp Asp Ala Ile Leu Ser Pro Gln
            180                 185                 190

Ile Met Tyr Gly Ser Ala Lys Ala Tyr Val Lys His Pro Ala Asp Ile
        195                 200                 205

Ala Pro Asp Tyr Leu Lys Leu Ser Phe Pro Glu Gly Phe Lys Trp
        210                 215                 220

Glu Arg Val Met Asn Phe Glu Asp Gly Gly Val Val His Val Asn Gln
225                 230                 235                 240

Ala Asp Ser Ser Leu Gln Asp Gly Val Phe Ile Ala Tyr Lys Val Lys
                245                 250                 255

Leu Arg Gly Thr Asn Phe Ala Pro Pro Asp Gly Pro Val Met Gln Lys
            260                 265                 270
```

```
Lys Ala Thr Met Gly Trp Glu Ala Thr Arg Asp Gln Leu Thr Glu Glu
            275                 280                 285

Glu Phe Arg Ala Ser Phe Asn His Phe Asp Arg Asp His Ser Gly Thr
        290                 295                 300

Leu Gly Pro Glu Glu Phe Lys Ala Cys Leu Ile Ser Leu Asp His Met
305                 310                 315                 320

Val Leu Leu Thr Thr Lys Glu Leu Gly Thr Val Met Arg Ser Leu Gly
                325                 330                 335

Gln Asn Pro Thr Glu Ala Glu Leu Gln Asp Met Ile Asn Glu Val Asp
            340                 345                 350

Ala Asp Gly Asp Gly Thr Phe Asp Phe Pro Glu Phe Leu Thr Met Met
        355                 360                 365

Ala Arg Lys Met Met Asn Asp Thr Asp Ser Glu Glu Glu Gly Val Gln
        370                 375                 380

Gly Thr Ser Glu Glu Glu Glu Leu Ala Asn Cys Phe Arg Ile Phe Asp
385                 390                 395                 400

Lys Asp Ala Asn Gly Phe Ile Asp Glu Glu Leu Gly Glu Ile Leu Arg
                405                 410                 415

Ala Thr Gly Glu His Val Thr Glu Glu Asp Ile Glu Asp Leu Met Lys
            420                 425                 430

Asp Ser Asp Lys Asn Asn Gly Arg Ile Asp Phe Gly Glu Lys Leu Thr
        435                 440                 445

Asp Glu Glu Val Phe Lys Glu Ala Phe Ser Leu Phe Asp Lys Asp Gly
        450                 455                 460

Asp Gly Thr Ile Thr Thr Lys Glu Leu Gly Thr Val Met Arg Ser Leu
465                 470                 475                 480

Glu Leu Asp Ala Ile Ile Glu Glu Val Asp Glu Asp Gly Ser Gly Thr
                485                 490                 495

Ile Asp Phe Glu Glu Phe Leu Val Met Met Val Arg Gln Gly Gln Asn
            500                 505                 510

Pro Thr Lys Glu Glu Leu Ala Asn Cys Phe Arg Ile Phe Asp Lys
        515                 520                 525

Asn Ala Asp Gly Phe Ile Asp Ile Glu Glu Leu Gly Glu Ile Leu Arg
530                 535                 540

Ala Thr
545

<210> SEQ ID NO 13
<211> LENGTH: 282
<212> TYPE: PRT
<213> ORGANISM: Artificial
<220> FEATURE:
<223> OTHER INFORMATION: recombinant voltage sensor with endosomal tag

<400> SEQUENCE: 13

Met Thr Ser Arg Lys Lys Val Leu Leu Lys Val Ile Ile Leu Gly Asp
1               5                   10                  15

Ser Gly Val Gly Lys Thr Ser Leu Met His Arg Tyr Val Asn Asp Met
            20                  25                  30

Ser Ser Val Arg Tyr Glu Gln Arg Glu Glu Pro Ser Met Val Asn Gly
        35                  40                  45

Asn Phe Gly Asn Thr Glu Glu Lys Val Glu Ile Asp Gly Asp Val Thr
    50                  55                  60

Ala Pro Pro Lys Ala Ala Pro Arg Lys Ser Glu Ser Val Lys Lys Val
65                  70                  75                  80
```

```
His Trp Asn Asp Val Asp Gln Gly Pro Asn Gly Lys Ser Glu Val Arg
                 85                  90                  95

Asn Glu Glu Arg Ile Asp Ile Pro Glu Ile Ser Ala Leu Trp Trp Gly
            100                 105                 110

Glu Asn Glu His Gly Ala Asp Asp Gly Arg Met Glu Leu Pro Ala Thr
            115                 120                 125

Met Trp Asn Lys Leu Arg Lys Val Ile Ser Pro Phe Val Met Ser Phe
130                 135                 140

Gly Phe Arg Val Phe Gly Val Val Leu Ile Ile Val Asp Phe Val Leu
145                 150                 155                 160

Val Ile Val Asp Leu Ser Val Thr Asp Lys Ser Ser Asn Ala Thr Thr
                165                 170                 175

Ala Ile Glu Ser Ile Ser Leu Ala Ile Ser Phe Phe Phe Leu Ile Asp
            180                 185                 190

Ile Ile Leu Arg Ile Phe Val Glu Gly Phe Asn Gln Tyr Phe Ser Ser
            195                 200                 205

Lys Leu Asn Ile Phe Asp Ala Ala Ile Val Ile Thr Leu Leu Val
210                 215                 220

Thr Leu Val Tyr Thr Val Leu Asp Ala Phe Thr Asp Phe Ser Gly Ala
225                 230                 235                 240

Thr Asn Ile Pro Arg Met Val Asn Phe Leu Arg Thr Leu Arg Ile Ile
                245                 250                 255

Arg Leu Val Arg Ile Phe Arg Leu Ala Ser Gln Lys Arg Glu Leu Arg
            260                 265                 270

Leu Ala Ser Arg Arg Thr Ile Ser Gln Asn
            275                 280

<210> SEQ ID NO 14
<211> LENGTH: 346
<212> TYPE: PRT
<213> ORGANISM: Artificial
<220> FEATURE:
<223> OTHER INFORMATION: recombinant ATP biosensor

<400> SEQUENCE: 14

Met Asp Tyr Lys Asp Asp Asp Lys Thr Asn Trp Gln Lys Arg
1               5                   10                  15

Ile Tyr Arg Val Lys Pro Cys Val Ile Cys Lys Val Ala Pro Arg Asp
            20                  25                  30

Trp Trp Val Glu Asn Arg His Leu Arg Ile Tyr Thr Met Cys Lys Thr
        35                  40                  45

Cys Phe Ser Asn Cys Ile Asn Tyr Gly Asp Asp Thr Tyr Tyr Gly His
    50                  55                  60

Asp Asp Trp Leu Met Tyr Thr Asp Cys Lys Glu Phe Ser Asn Thr Tyr
65                  70                  75                  80

His Asn Leu Gly Arg Leu Pro Asp Glu Asp Arg His Trp Ser Ala Ser
                85                  90                  95

Cys His His His His His Met Gly Met Ser Gly Ser Met Val Ser
            100                 105                 110

Lys Gly Glu Glu Leu Ile Lys Glu Asn Met Arg Met Lys Val Val Met
            115                 120                 125

Glu Gly Ser Val Asn Gly His Gln Phe Lys Cys Thr Gly Glu Gly Glu
            130                 135                 140

Gly Asn Pro Tyr Met Gly Thr Gln Thr Met Arg Ile Lys Val Ile Glu
145                 150                 155                 160
```

-continued

```
Gly Gly Pro Leu Pro Phe Ala Phe Asp Ile Leu Ala Thr Ser Phe Met
            165                 170                 175

Tyr Gly Ser Arg Thr Phe Ile Lys Tyr Pro Lys Gly Ile Pro Asp Phe
            180                 185                 190

Phe Lys Gln Ser Phe Pro Glu Gly Phe Thr Trp Glu Arg Val Thr Arg
            195                 200                 205

Tyr Glu Asp Gly Gly Val Val Thr Val Met Gln Asp Thr Ser Leu Glu
            210                 215                 220

Asp Gly Cys Leu Val Tyr His Val Gln Val Arg Gly Val Asn Phe Pro
225                 230                 235                 240

Ser Asn Gly Pro Val Met Gln Lys Lys Thr Lys Gly Trp Glu Pro Asn
            245                 250                 255

Thr Glu Met Met Tyr Pro Ala Asp Gly Gly Leu Arg Gly Tyr Thr His
            260                 265                 270

Met Ala Leu Lys Val Asp Gly Gly His Leu Ser Cys Ser Phe Val
            275                 280                 285

Thr Thr Tyr Arg Ser Lys Lys Thr Val Gly Asn Ile Lys Met Pro Gly
            290                 295                 300

Ile His Ala Val Asp His Arg Leu Glu Arg Leu Glu Glu Ser Asp Asn
305                 310                 315                 320

Glu Met Phe Val Val Gln Arg Glu His Ala Val Ala Lys Phe Ala Gly
            325                 330                 335

Leu Gly Gly Gly Met Asp Glu Leu Tyr Lys
            340                 345

<210> SEQ ID NO 15
<211> LENGTH: 442
<212> TYPE: PRT
<213> ORGANISM: Artificial
<220> FEATURE:
<223> OTHER INFORMATION: recombinant heme biosensor

<400> SEQUENCE: 15

Met Ala Ala Met Leu Glu Pro Glu Pro Val Val Ala Glu Gly Thr Ala
1               5                   10                  15

Ala Gln Ala Val Glu Thr Pro Asp Trp Glu Ala Pro Glu Asp Ala Gly
            20                  25                  30

Ala Gln Pro Gly Ser Tyr Glu Ile Arg His Tyr Gly Pro Ala Lys Trp
            35                  40                  45

Val Ser Thr Cys Val Glu Ser Met Asp Trp Asp Ser Ala Val Gln Thr
        50                  55                  60

Gly Phe Thr Lys Leu Asn Ser Tyr Ile Gln Gly Lys Asn Glu Lys Gly
65                  70                  75                  80

Met Lys Ile Lys Met Thr Ala Pro Val Leu Ser Tyr Val Glu Pro Gly
            85                  90                  95

Pro Gly Pro Phe Ser Glu Ser Thr Ile Thr Ile Ser Leu Tyr Ile Pro
            100                 105                 110

Ser Glu Gln Gln Ser Asp Pro Pro Arg Pro Ser Glu Ser Asp Val Phe
            115                 120                 125

Ile Glu Asp Arg Ala Lys Met Thr Val Phe Ala Arg Cys Phe Glu Gly
            130                 135                 140

Phe Cys Ser Ala Gln Lys Asn Gln Glu Gln Leu Leu Thr Leu Ala Ser
145                 150                 155                 160

Ile Leu Arg Glu Glu Gly Lys Val Phe Asp Glu Lys Val Phe Tyr Thr
            165                 170                 175
```

```
Ala Gly Tyr Asn Ser Pro Phe Arg Leu Leu Asp Lys Asn Asn Glu Val
            180                 185                 190

Trp Leu Ile Gln Lys Asn Lys Pro Phe Lys Ala Asn Glu Met Val Ser
        195                 200                 205

Lys Gly Glu Glu Leu Ile Lys Glu Asn Met Arg Met Lys Val Val Met
    210                 215                 220

Glu Gly Ser Val Asn Gly His Gln Phe Lys Cys Thr Gly Glu Gly Glu
225                 230                 235                 240

Gly Asn Pro Tyr Met Gly Thr Gln Thr Met Arg Ile Lys Val Ile Glu
                245                 250                 255

Gly Gly Pro Leu Pro Phe Ala Phe Asp Ile Leu Ala Thr Ser Phe Met
            260                 265                 270

Tyr Gly Ser Arg Thr Phe Ile Lys Tyr Pro Lys Gly Ile Pro Asp Phe
        275                 280                 285

Phe Lys Gln Ser Phe Pro Glu Gly Phe Thr Trp Glu Arg Val Thr Arg
    290                 295                 300

Tyr Glu Asp Gly Gly Val Val Thr Val Met Gln Asp Thr Ser Leu Glu
305                 310                 315                 320

Asp Gly Cys Leu Val Tyr His Val Gln Val Arg Gly Val Asn Phe Pro
                325                 330                 335

Ser Asn Gly Pro Val Met Gln Lys Lys Thr Lys Gly Trp Glu Pro Asn
            340                 345                 350

Thr Glu Met Met Tyr Pro Ala Asp Gly Gly Leu Arg Gly Tyr Thr His
        355                 360                 365

Met Ala Leu Lys Val Asp Gly Gly His Leu Ser Cys Ser Phe Val
    370                 375                 380

Thr Thr Tyr Arg Ser Lys Lys Thr Val Gly Asn Ile Lys Met Pro Gly
385                 390                 395                 400

Ile His Ala Val Asp His Arg Leu Glu Arg Leu Glu Glu Ser Asp Asn
                405                 410                 415

Glu Met Phe Val Val Gln Arg Glu His Ala Val Ala Lys Phe Ala Gly
            420                 425                 430

Leu Gly Gly Gly Met Asp Glu Leu Tyr Lys
        435                 440

<210> SEQ ID NO 16
<211> LENGTH: 571
<212> TYPE: DNA
<213> ORGANISM: Homo sapiens

<400> SEQUENCE: 16
cctgcagggc ccactagtat ctgcagaggg ccctgcgtat gagtgcaagt gggttttagg      60
accaggatga ggcggggtgg gggtgcctac ctgacgaccg accccgaccc actggacaag     120
cacccaaccc ccattcccca aattgcgcat cccctatcag agaggggag gggaaacagg     180
atgcggcgag gcgcgtgcgc actgccagct tcagcaccgc ggacagtgcc ttcgcccccg     240
cctggcggcg cgcgccaccg ccgcctcagc actgaaggcg cgctgacgtc actcgccggt     300
cccccgcaaa ctccccttcc cggccacctt ggtcgcgtcc gcgccgccgc cggcccagcc     360
ggaccgcacc acgcgaggcg cgagataggg gggcacgggc gcgaccatct cgctgcggc     420
gccggcgact cagcgctgcc tcagtctgcg gtgggcagcg gaggagtcgt gtcgtgcctg     480
agagcgcagc tgtgctcctg ggcaccgcgc agtccgcccc cgcggctcct ggccagacca     540
cccctaggac cccctgcccc aagtcgcagc c                                    571
```

<210> SEQ ID NO 17
<211> LENGTH: 190
<212> TYPE: PRT
<213> ORGANISM: Homo sapiens

<400> SEQUENCE: 17

Met Asp Cys Leu Cys Ile Val Thr Thr Lys Lys Tyr Arg Tyr Gln Asp
1               5                   10                  15

Glu Asp Thr Pro Pro Leu Glu His Ser Pro Ala His Leu Pro Asn Gln
            20                  25                  30

Ala Asn Ser Pro Pro Val Ile Val Asn Thr Asp Thr Leu Glu Ala Pro
        35                  40                  45

Gly Tyr Glu Leu Gln Val Asn Gly Thr Glu Gly Met Glu Tyr Glu
    50                  55                  60

Glu Ile Thr Leu Glu Arg Gly Asn Ser Gly Leu Gly Phe Ser Ile Ala
65                  70                  75                  80

Gly Gly Thr Asp Asn Pro His Ile Gly Asp Asp Pro Ser Ile Phe Ile
                85                  90                  95

Thr Lys Ile Ile Pro Gly Gly Ala Ala Ala Gln Asp Gly Arg Leu Arg
            100                 105                 110

Val Asn Asp Ser Ile Leu Phe Val Asn Glu Val Asp Val Arg Glu Val
        115                 120                 125

Thr His Ser Ala Ala Val Glu Ala Leu Lys Glu Ala Gly Ser Ile Val
    130                 135                 140

Arg Leu Tyr Val Met Arg Arg Lys Pro Pro Ala Glu Lys Val Met Glu
145                 150                 155                 160

Ile Lys Leu Ile Lys Gly Pro Lys Gly Leu Gly Phe Ser Ile Ala Gly
                165                 170                 175

Gly Val Gly Asn Ser Thr Ser Leu Glu Ile Thr Ala Ser Met
            180                 185                 190

<210> SEQ ID NO 18
<211> LENGTH: 109
<212> TYPE: PRT
<213> ORGANISM: Homo sapiens

<400> SEQUENCE: 18

Met Asp Tyr Lys Asp Asp Asp Lys Thr Asn Trp Gly Lys
1               5                   10                  15

Arg Ile Tyr Arg Val Lys Pro Cys Val Ile Cys Lys Val Ala Pro
            20                  25                  30

Arg Asp Trp Trp Val Glu Asn Arg His Leu Arg Ile Tyr Thr Met
        35                  40                  45

Cys Lys Thr Cys Phe Ser Asn Cys Ile Asn Tyr Gly Asp Asp Thr
    50                  55                  60

Tyr Tyr Gly His Asp Asp Trp Leu Met Tyr Thr Asp Cys Lys Glu
65                  70                  75

Phe Ser Asn Thr Tyr His Asn Leu Gly Arg Leu Pro Asp Glu Asp
                80                  85                  90

Arg His Trp Ser Ala Ser Cys His His His His His Met Gly
            95                  100                 105

Met Ser Gly Ser

<210> SEQ ID NO 19
<211> LENGTH: 237
<212> TYPE: PRT

```
<213> ORGANISM: Artificial
<220> FEATURE:
<223> OTHER INFORMATION: recombinant fluorescent reporter domain

<400> SEQUENCE: 19

Met Val Ser Lys Gly Glu Glu Leu Ile Lys Glu Asn Met Arg Met
1               5                   10                  15

Lys Val Val Met Glu Gly Ser Val Asn Gly His Gln Phe Lys Cys
                20                  25                  30

Thr Gly Glu Gly Glu Gly Asn Pro Tyr Met Gly Thr Gln Thr Met
                35                  40                  45

Arg Ile Lys Val Ile Glu Gly Gly Pro Leu Pro Phe Ala Phe Asp
                50                  55                  60

Ile Leu Ala Thr Ser Phe Met Tyr Gly Ser Arg Thr Phe Ile Lys
                65                  70                  75

Tyr Pro Lys Gly Ile Pro Asp Phe Phe Lys Gln Ser Phe Pro Glu
                80                  85                  90

Gly Phe Thr Trp Glu Arg Val Thr Arg Tyr Glu Asp Gly Gly Val
                95                  100                 105

Val Thr Val Met Gln Asp Thr Ser Leu Glu Asp Gly Cys Leu Val
                110                 115                 120

Tyr His Val Gln Val Arg Gly Val Asn Phe Pro Ser Asn Gly Pro
                125                 130                 135

Val Met Gln Lys Lys Thr Lys Gly Trp Glu Pro Asn Thr Glu Met
                140                 145                 150

Met Tyr Pro Ala Asp Gly Gly Leu Arg Gly Tyr Thr His Met Ala
                155                 160                 165

Leu Lys Val Asp Gly Gly His Leu Ser Cys Ser Phe Val Thr
                170                 175                 180

Thr Tyr Arg Ser Lys Lys Thr Val Gly Asn Ile Lys Met Pro Gly
                185                 190                 195

Ile His Ala Val Asp His Arg Leu Glu Arg Leu Glu Glu Ser Asp
                200                 205                 210

Asn Glu Met Phe Val Val Gln Arg Glu His Ala Val Ala Lys Phe
                215                 220                 225

Ala Gly Leu Gly Gly Gly Met Asp Glu Leu Tyr Lys
                230                 235
```